United States Patent [19]
Garfield et al.

[11] Patent Number: 5,895,783
[45] Date of Patent: Apr. 20, 1999

[54] TREATMENT OF PREECLAMPSIA AND PRETERM LABOR WITH COMBINATION OF PROGESTATIONAL AGENT AND A NITRIC OXIDE SYNTHASE SUBSTRATE AND/OR DONOR

[75] Inventors: Robert E. Garfield, Friendswood, Tex.; Krzysztof Chwalisz; Radoslaw Bukowski, both of Berlin, Germany; Chandra Yallampal Li, Houston, Tex.

[73] Assignees: Schering Aktiengesellschaft, Germany; The University of Texas, Austin, Tex.

[21] Appl. No.: 08/092,426

[22] Filed: Jul. 16, 1993

[51] Int. Cl.$^6$ .................. A61K 38/60; A61K 31/195; A01N 37/12; A01N 43/58

[52] U.S. Cl. .................. 514/12; 514/21; 514/177; 514/178; 514/179; 514/180; 514/181; 514/182; 514/258; 514/263; 514/307; 514/412; 514/509; 514/561; 514/562; 514/565; 514/608; 514/645; 424/608

[58] Field of Search .................. 514/12, 21, 412, 514/561, 263, 509, 562, 258, 307, 608, 567, 177–182, 645; 424/608

[56] References Cited

U.S. PATENT DOCUMENTS

| | | | |
|---|---|---|---|
| 5,217,997 | 6/1993 | Levere et al. | 514/565 |
| 5,508,045 | 4/1996 | Harrison et al. | 424/608 |

FOREIGN PATENT DOCUMENTS

| | | |
|---|---|---|
| 0 441 119 | 8/1991 | European Pat. Off. . |

| | | |
|---|---|---|
| WO 95/22345 | 8/1995 | WIPO . |

OTHER PUBLICATIONS

Bayhi et al., J. Clin. Anesth., 4:487–488 (1992).
Conrad, FASEB, 7:566–571 (1993).
Diamond, J. Pharm. & Exp. Thera., 168(1):21–30 (1969).
Yallampalli et al., Soc. Gynecol. Invest. Abst. P41 (1993).
Yallampalli et al., Am. J. Obstet. Gynecol., 169:1316–1320 (1993).
Yallampalli et al., Am. J. Obstet. Gynecol., 170:175–185 (1993).
Greenspoon et al., Lancet, 338:124 (1991).
Jennings et al., J. of Mat. Fetal Med., 2:170–175 (1993).
Natuzzi et al., Biochem. & Biophys. Res. Comm., 194(1):1–8 (1993).
Papka et al., Neuroscience Letters, 147:224–228 (1992).
Sladek et al., Am. J. Obstet. Gynecol., 169:1285–1291 (1993).
Yallampalli et al., Endocrinology, 133(4):1899–1904 (1993).

*Primary Examiner*—Herbert J. Lilling
*Attorney, Agent, or Firm*—Millen, White, Zelano & Branigan, P.C.

[57] ABSTRACT

Preeclampsia and preterm labor in a pregnant female mammal are treated by administering thereto a combination of a progestin and a nitric oxide synthase substrate, a nitric oxide donor or both, optionally in further combination with one or more of a cyclooxygenase inhibitor, a $PGI_2$-mimetic, a thromboxane ($TXA_2$) inhibitor, a compound possessing $TXA_2$-agonistic and $TXA_2$-inhibiting properties, a compound possessing $TXA_2$-antagonistic and $PGI_2$-memetic activities, and a $TXA_2$ antagonist.

22 Claims, 6 Drawing Sheets

TREATMENT OF PREECLAMPSIA AND PRETERM LABOR WITH COMBINATION OF PROGESTATIONAL AGENT AND A NITRIC OXIDE SYNTHASE SUBSTRATE AND/OR DONOR

BACKGROUND OF THE INVENTION

This invention relates to a method for the treatment of preeclampsia and of preterm labor with the combination of a progestational agent and a nitric oxide synthase substrate, a nitric oxide donor or both, alone or in further combination with one or more of a cyclooxygenase inhibitor, a $PGI_2$-mimetic, a thromboxane ($TXA_2$) inhibitor, A compound possessing $TXA_2$-agonistic and $TXA_2$-inhibiting properties, a compound possessing $TXA_2$ antagonistic and $PGI_2$-memetic activities, and a $TXA_2$ antagonist, and to pharmaceutical compositions comprising such a combination.

Preeclampsia, toxemia or eclampsia of pregnancy can be a significant health problem during pregnancy and they are the leading causes of fetal growth retardation, fetal mortality and morbidity, premature birth and maternal mortality. The etiology of the disease is largely unknown and effective therapy is not available. Preeclampsia of pregnancy is characterized by a triad of hypertension, pathological edema and proteinuria. This disease affects 6 to 10% of all pregnancies.

Recently, nitric oxide has been shown to be endothelium derived relaxing factor (EDRF) from the endothelium of blood vessels. Nitric oxide is considered to be a major mediator in the control of vascular reactivity. Nitric oxide is synthesized from L-arginine by nitric oxide synthase located in endothelial cells. Nitric Oxide can also be generated by application of various nitric oxide donors such as sodium nitroprusside, nitroglycerin, glyceryl trinitrite, SIN-1, isosorbid mononitrite, isosorbid dinitrite, etc.

Treatment of pregnant rats with nitric oxide synthase inhibitors, which are analogues of L-arginine (such as L-NAME, $N^G$-nitro-L-arginine methyl ester) results in elevated blood pressure, fetal retarded growth and proteinuria. Thus, inhibition of nitric oxide synthesis produces conditions and symptoms identical to preeclampsia of pregnancy and establishes that preeclampsia is the direct result of the decrease in nitric oxide synthesis and/or a change in the regulation of vascular tone. These conditions give rise to increased blood pressure, decreased blood flow to the fetus, retarded fetal development and proteinuria. Agents which raise nitric oxide levels therefore are useful in the treatment of preeclampsia of pregnancy. Since nitric oxide donors also reduce contractility of the uterus during pregnancy, nitric oxide donors are also useful for use in preterm labor.

The nitric oxide effects on smooth muscle depend upon the activation of guanylate cyclase and generation of cGMP to produce relaxation and this step is progesterone dependent. Thus, combinations of nitric oxide donors with progesterone are particularly efficacious for the treatment of preeclampsia and of preterm labor.

EP 0 441 119 A2 discloses the use of L-arginine in the treatment of hypertension and other vascular disorders. It suggests that the mechanism by which L-arginine is effective for this purpose is because it may be the physiological precursor of "the most powerful endothelial-derived releasing factor, nitric oxide." The use of L-arginine in combination with other pharmaceutically active agents is not discussed in this publication.

OBJECTS OF THE INVENTION

It is an object of the invention to provide a method for the prevention and treatment of preeclampsia with a combination of a progestational agent and a nitric oxide substrate and/or donor.

It is another object to provide such a method in which a progestational agent is used in combination with a nitric oxide substrate and/or donor for the prevention and treatment of preeclampsia.

It is a further object to provide a method for the prevention and treatment of preterm labor using a progestational agent in combination with a nitric oxide substrate and/or donor.

A further object is the provision of pharmaceutical compositions useful in practicing the methods of this invention.

Other objects will be apparent to those skilled in the art to which this invention pertains.

SUMMARY OF THE INVENTION

In a method aspect, this invention relates to a method of treating at least one of preeclampsia and preterm labor in a pregnant female which comprises administering to a pregnant female manifesting the symptoms thereof, (a) a progestational agent and (b) one or both of a nitric oxide synthase substrate and a nitric oxide donor, alone or in further combination with one or more of a cyclooxygenase inhibitor, a $PGI_2$-mimetic, a thromboxane ($TXA_2$) inhibitor, a compound possessing $TXA_2$-agonistic and $TXA_2$-inhibiting properties, a compound possessing $TXA_2$-antagonistic and $PGI_2$-memetic activities, and a $TXA_2$ antagonist, in amounts effective to ameliorate the symptoms thereof, the amount of the progestational agent administered being bioequivalent to 50-300 mg. of injected progesterone and the amount of the nitric oxide synthase substrate, nitric oxide donor or both being effective to, respectively, either raise the blood level of circulating L-arginine in a pregnant female to whom the composition is administered to at least about 1 mmole above the normally 2 to 3 mmolar circulating levels or raise nitric oxide donor levels to about 1 to 100 nmolar (nanamolar).

In another method aspect, this invention relates to a method of treating preterm labor in a pregnant female which comprises administering to a pregnant female manifesting the symptoms thereof, amounts of (a) a progestational agent and (b) at least one of a nitric oxide synthase substrate and a nitric oxide donor effective to terminate the preterm labor, alone or in further combination with one or more of a cyclooxygenase inhibitor, a $PGI_2$-mimetic, a thromboxane ($TXA_2$) inhibitor, a compound possessing $TXA_2$-agonistic and $TXA_2$-inhibiting properties, a compound possessing $TXA_2$-antagonistic and $PGI_2$-memetic activities, and a $TXA_2$ antagonist, the amount of the progestational agent administered being bioequiva-lent to 50-300 mg. of injected progesterone and the amount of the nitric oxide synthase substrate, nitric oxide donor or both being effective to, respectively, either raise the blood level of circulating L-arginine in a pregnant female to whom the composition is administered to at least about 1 mmole above the normally 2 to 3 mmolar circulating levels, or raise nitric oxide donor levels to about 1 to 100 nmolar.

In a product aspect, this invention relates to a pharmaceutical composition comprising (a) a progestational agent and (b) at least one of a nitric oxide synthase substrate and a nitric oxide donor, alone or in further combination with one or more of a cyclooxygenase inhibitor, a $PGI_2$-mimetic, a thromboxane ($TXA_2$) inhibitor, a compound possessing $TXA_2$-agonistic and $TXA_2$-inhibiting properties, a compound possessing $TXA_2$-antagonistic and $PGI_2$-memetic activities, and a $TXA_2$ antagonist, with the amount of the progestational agent per unit dosage being bioequivalent to 50–300 mg. of injected progesterone and the amount of the nitric oxide synthase substrate, a nitric oxide donor or both per unit dosage being effective to, repsectively, either raise the blood level of circulating L-arginine to at least about 1 mmole above the normally 2 to 3 mmolar circulating levels or raise the nitric oxide donor levels to about 1 to 1000 nmolar.

DETAILED DISCLOSURE

The methods of this invention treat one or more of preeclampsia and preterm labor in a pregnant female mammal, preferably a human, who is manifesting the symptoms thereof or who is a high risk candidate for doing so, e.g., as determined by the progress of a present or previous pregnancy.

Because these abnormal conditions of pregnancy are produced by or aggravated by subnormal nitric oxide synthesis, both nitric oxide synthase substrates, e.g., L-arginine, and nitric oxide donors, e.g., sodium nitroprusside, nitroglycerin, glyceryl trinitrate, SIN-1, isosobid mononitrate and isosorbid dinitrate, are useful for ameliorating the symptoms thereof and, in one aspect of the method of this invention, a combination of both are employed.

A synergistic effect is achieved when a progestational agent is administered concurrently with the nitric oxide substrate and/or nitric acid donor.

Thus, the method aspect of this invention and the pharmaceutical composition aspect of this invention employs a combination of (a) a progestational agent, e.g., progesterone, and (b) either or both of a nitric oxide donor and a nitric oxide synthase substrate and, optionally, (c) one or more of a cyclooxygenase inhibitor, e.g., aspirin; a PGI$_2$-mimetic, e.g., iloprost and cicaprost; a thromboxane (TXA$_2$) inhibitor, e.g., dazoxiben hydrochloride (benzoic acid, 4-[2-(1H-imadazol1-yl)-ethoxy]-, monohydrochloride; UK 37248), dazmegrel (1H-indole-1-propanoic acid, 3-(1H-imidazol-1-ylmethyl)-2-methyl-; UK 3885), ozagrel (2-propenoic acid, 3-[4-(1-H-imidazol-1-ylmethyl)phenyl]-; OKY-046) and pirmagrel (imidazol1,5-a|pryidine-5-hexanoic acid; CGS-13080); a compound possessing TXA$_2$-agonistic and TXA$_2$-inhibiting properties, e.g., ridogrel (pentanoic acid, 5-[[[3-pyri-dinyl[3-(trifluoromethyl)phenyl]methylene]-amino]oxy]-; R-68070) and labogrel (6-heptenoic acid, 7-phenyl-7-(3-pydridinyl)-; a compound possessing TXA-antagonistic and PGI$_2$-memetic activities, e.g., 5-heptenoic acid, 7-[3-[[(diphenylmethoxy)-imino]-bicyclo,[2.2.1]hept-2-yl]-; EP 035-rac) and 5-heptenoic acid, 7-[3-[[(diphenylmethoxy)-imino]methyl]biclo[2.2.2]-oct-5-en-2-yl]- (EP 157); and a TXA$_2$ antagonist, e.g., 5-heptenoic acid, 7-[3-[[2-(phenyl-amino)carbonyl]-hydrazino]methyl]7-oxabicyclo[2.2.1]hept-2-yl]-, 1S[1.alpha.,2.alpha.(Z), 3.alpha.,4.alpha.]]- (SQ 29548); benzenepropanoic acid, 2-[[3-4[(pentylamino)carbonyl]-2-oxazolyl]-7-oxabicyclo [2.2.1]hept-2-ylmethyl}- (BMS 180291); acetic acid, [4-[2-[(phenylsulfonyl)amino]-ethyl]penoxy]- (sultroban, BM-13177); benzeneacetic acid, 4-[2-[[(4-chlorophenyl) sulfonyl]amino]ethyl]- (daltroban, BM-13505); (S-145 rac); 5-hexenoic acid, 6-[3-[[(4-bromophenyl)sulfonyl]amino] methyl]bicyclo[2.2.1)hep-2-yl]-, decyl ester, [1S [1.alpha.2.alpha.2.alpha.(Z),- 3.beta.,4.alpha.]]- (ONO 8809); 9H-carbazole-9-propanoic acid, 3-[[(4-fluorophenyl) sulfonyl]amino]-1,2,3,4-tetra-hydro-, (R)- (bay-u-3405); and (4Z)-6-[(5S)-5-(4-chlor-phenylsulfonyl(aminomethyl)-cycloent-1-enyl]4-hexenoic acid (ZU 154343).

Examples of combinations of active agents which can be administered concurrently with a nitric oxide substrate and/or a nitric oxide donor and a progesterone (or other progestational agent) are low dose (e.g.,10–100 mg) of aspirin (or other cyclooxygenase inhibitor; PGI$_2$-mimetics (e.g., iloprost, cicaprost); combinations of a PGI$_2$-mimetic and low dose aspirin.

Examples of dosage ranges of typical NO-substrates and NO-donors (per os) are:

| | total dose: | |
|---|---|---|
| L-Arginine | 500 | mg-10 g p.o. |
| Sodium Nitroprusside | range 500–2000 | ug/kg/day |
| Nitroglycerin | 0.5–10 | mg |
| Isosorbid mononitrate | 10–100 | mg |
| Isosorbid dinitrate | 10–100 | mg |

The following are typical oral dosage ranges active agents of the progestin and the optional other active agents concurrently administered with the nitric oxide substrate or donor:

Progestins: A daily dose bioequivalent to 50–300 mg of progesterone/day, e.g., an injectable suspension of medroxyprogersterone acetate to provide a weekly dose of thereof of 100–1000 mg or tablets or dragees providing an oral dose thereof of 5–10 mg/day; an injectable solution of hydroxyprogesterone caproate which provides a weekly dose of 250–500 mg; tablets, capsules or dragees of northindrone acetate which provide a daily dose of 5–20 mg.

Cicaprost: 5–100 ug/kg/day p.o.

Aspirin: 10–100 mg/kg/day p.o.

The pharmacologically active agents employed in this invention can be administered in admixture with conventional excipients, i.e., pharmaceutically acceptable liquid, semi-liquid or solid organic or inorganic carriers suitable, e.g., for parental or enteral application and which do not deleteriously react with the active compound in admixture therewith. Suitable pharmaceutically acceptable carriers include but are not limited to water, salt solutions, alcohols, vegetable oils, polyethylene glycols, gelatin, lactose, amylose, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are solutions, preferably oily or aqueous solutions, as well as suspensions, emulsions, or implants, including suppositories. Ampoules are convenient unit dosages.

In a preferred aspect, the composition of this invention is adapted for ingestion.

For enteral application, particularly suitable are unit dosage forms, e.g., tablets, dragees or capsules having talc and/or a carbohydrate carrier or binder or the like, the carrier preferably being lactose and/or corn starch and/or potato starch; particulate solids, e.g., granules; and liquids and semi-liquids, e.g., syrups and elixirs or the like, wherein a sweetened vehicle is employed. Sustained release compositions can be formulated including those wherein the active compound is protected with differentially degradable coatings, e.g., by micro-encapsulation, multiple coatings, etc.

Suitable for oral administration are, inter alia, tablets, dragees, capsules, pills, granules, suspensions and solutions. Each unit dose, e.g., each tablespoon of liquid or each tablet, or dragee contains, for example, 5–5000 mg of each active agent.

Solutions for parenteral administration contain, for example, 0.01 –1% of each active agent in an aqueous or alcoholic solution.

The nitric oxide substrate and/or donor can be administered as an admixture with the progestational agent and any other optional active agent or as a separate unit dosage form, either simultaneously there-with or at different times during the day from each other.

The combination of active agents is preferably administered at least once daily (unless administered in a dosage form which delivers the active agents continuously) and more preferably several times daily, e.g., in 2 to 6 divided doses. The typical dose is about 0.5 to 1000 mg of each active agent, although some less active agents, e.g., L-Arginine, require much higher oral dosages, e.g., 500 to 10,000 mg, and others, e.g., sodium nitroprusside, require lower doses, e.g., 500–2,000 ug/kg/day. Doses for nitroglycerine typically are orally 2.5 mg 2×daily; sublingually, 0.8 mg 1–4×daily; and transdermally, 0.2–0.4 mg/hr. Since the $LD_{50}$ dosages of most of these active agents is known in the prior art, a lower dosage regimen can be initiated and the dosage increased until a positive effect is achieved or a higher dosage regimen can initially be employed, e.g., in a crisis situation, and the dosages regulated downward as relief from the symptoms is achieved.

In humans, both L-arginine and progesterone (or bioequivalent of another progestin) should be given in a ratio which produces blood plasma levels of about 1–5 mMol/ml and 300–1,000 ng/ml (0.9–3 µMol/l), respectively. The NO-donor, e.g., sodium nitroprusside, should be given with the progesterone (or bioequivalent of another progestin) in a ratio producing blood plasma levels of about 1–10 µMol/l and 300–1,000 ng/ml (0.9–3 µMol/l), respectively.

DISCUSSION OF THE DRAWINGS

Figure 1:
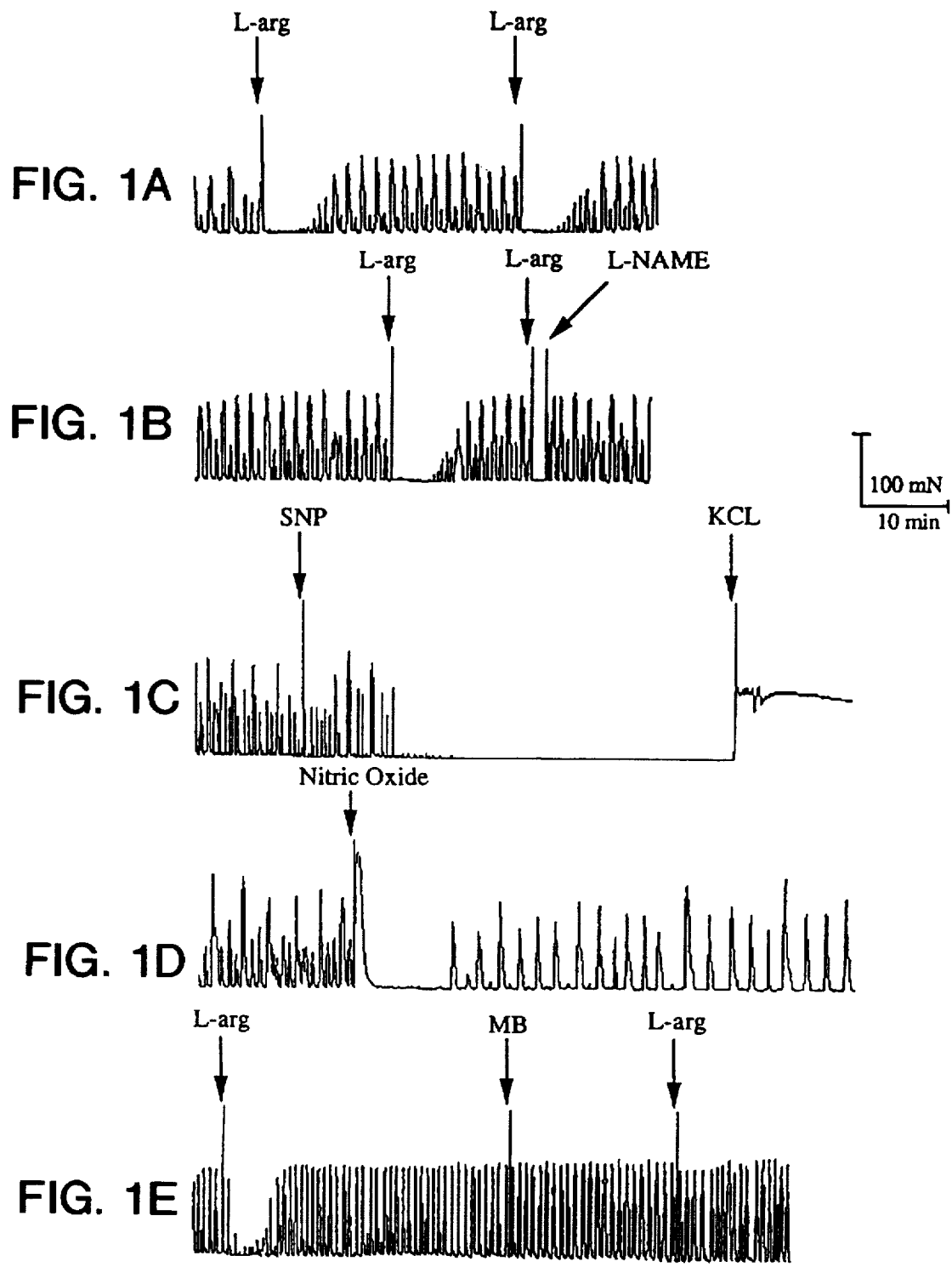
FIG. 1 is a series of strip chart recordings showing the effect of L-arginine on spontaneously contracting uterine strips from rat on day 18 of gestation.

The strip chart recordings of FIG. 1 show that the application of L-arginine (1–3 mM) (A, B, E), sodium nitroprusside (5 mM)(C), nitric oxide (0.1 mM) (D) to muscle baths produced substantial relaxations. The effects of L-arginine were reversed by L-NAME (3 mM)(B) and methylene blue (0. mM)(E). These are typical recordings of 8–16 strips from 6 animals in each group. Each upstroke from baseline represents a contraction.

The strip chart recording of FIG. 1C shows that the application of sodium nitroprusside (SNP) caused sustained relaxation in spontaneously contracting uterine strips after a lag period and that tissues in the relaxed state were responsive to potassium chloride. Similar recordings of 12 uterine strips from 4 animals were obtained.

The strip chart recording in FIG. 1D shows the relaxation produced by authentic nitric oxide gas (0.1 mM). Similar recordings were obtained from 8 strips from 4 animals.

The strip chart recordings of FIG. 1E show that L-arginine (1 mM) produced relaxation of spontaneously contracting tissues and these effects were repeatable in the same strip (as in FIG. 1A) and that the relaxation effect of L-arginine (1 mM) was abolished by methylene blue (0.1 mM) when added before the application of L-arginine (B).

Figure 2:
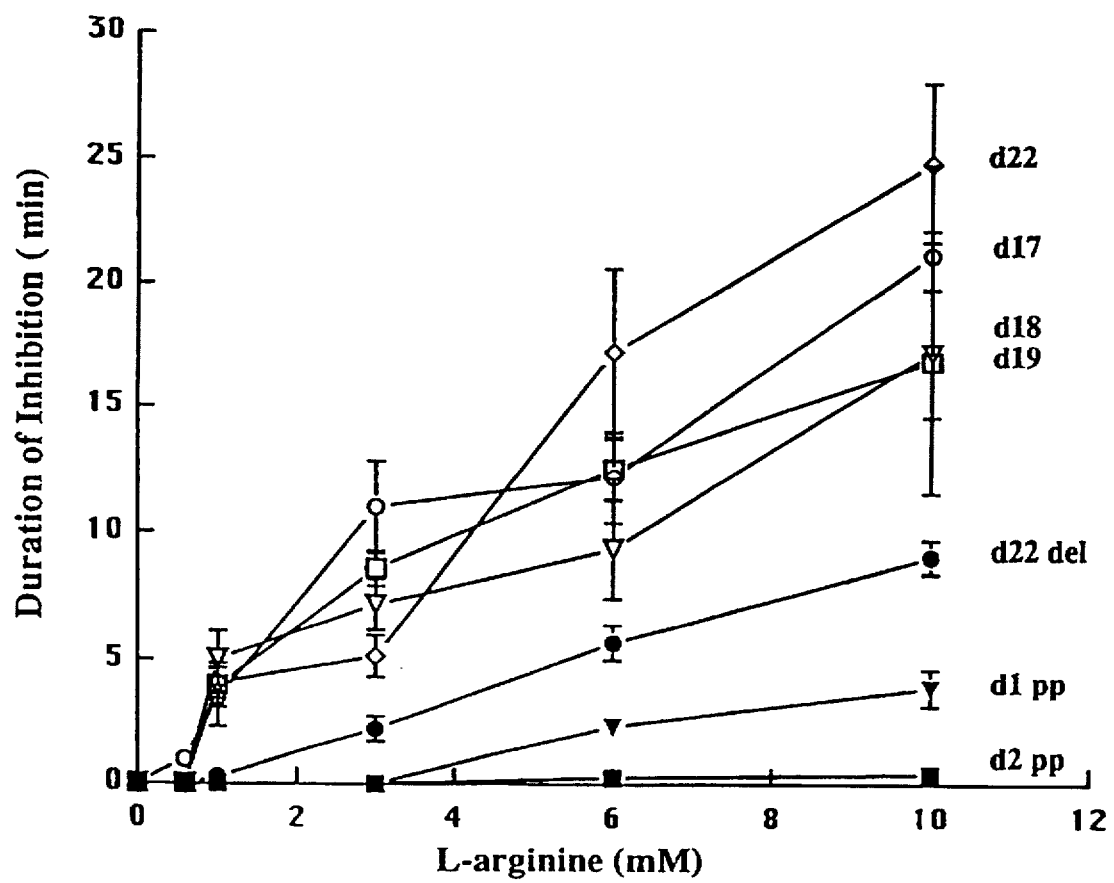
FIG. 2: Dose-dependent relaxation effects of L-arginine (0.1 mM to 10 mM) on spontaneously contracting uterine strips from rats at different stages of gestation, during delivery and post partum. The tissues were obtained on days 17–22 (d17, d18, d19 and d22) of gestation, on day 22 (d22 del) during spontaeous delivery (1–3 pups delivered), or on 1 (d1pp) and 2 (d2pp) days postpartum. The duration of complete inhibition of spontaneous uterine contractions are dose-dependent. Data are analyzed by repeated measures ANOVA on seven groups. The effects of L-arginine from concentrations of 1 mM are significantly (P<0.01) decreased during spontaneous delivery at term and postpartum, compared to all other times. Each data point represents mean ± S.E.M. The total number of strips studied at each time period was 8–16 from 4–6 animals per group.

In the experiments whose results are shown by the graph of FIG. 2, the tissues were obtained on days 17–22 (d17, d18, d19 and d22) of gestation, on day 22 (d22 del) during spontaneous delivery (1–3 pups delivered), or on 1 (d1pp) and 2 (d2pp) days postpartum. The duration of complete inhibition of spontaneous uterine contractions are dose-dependent. The effects of L-arginine from concentrations of 1 mM are significantly (P<0.01) decreased during spontaneous delivery at term and postpartum, compared to all other times. Each data point represents mean ± S.E.M. The total number of strips studied at each time period was 8–16 from 4–6 animals per group.

Figure 3:
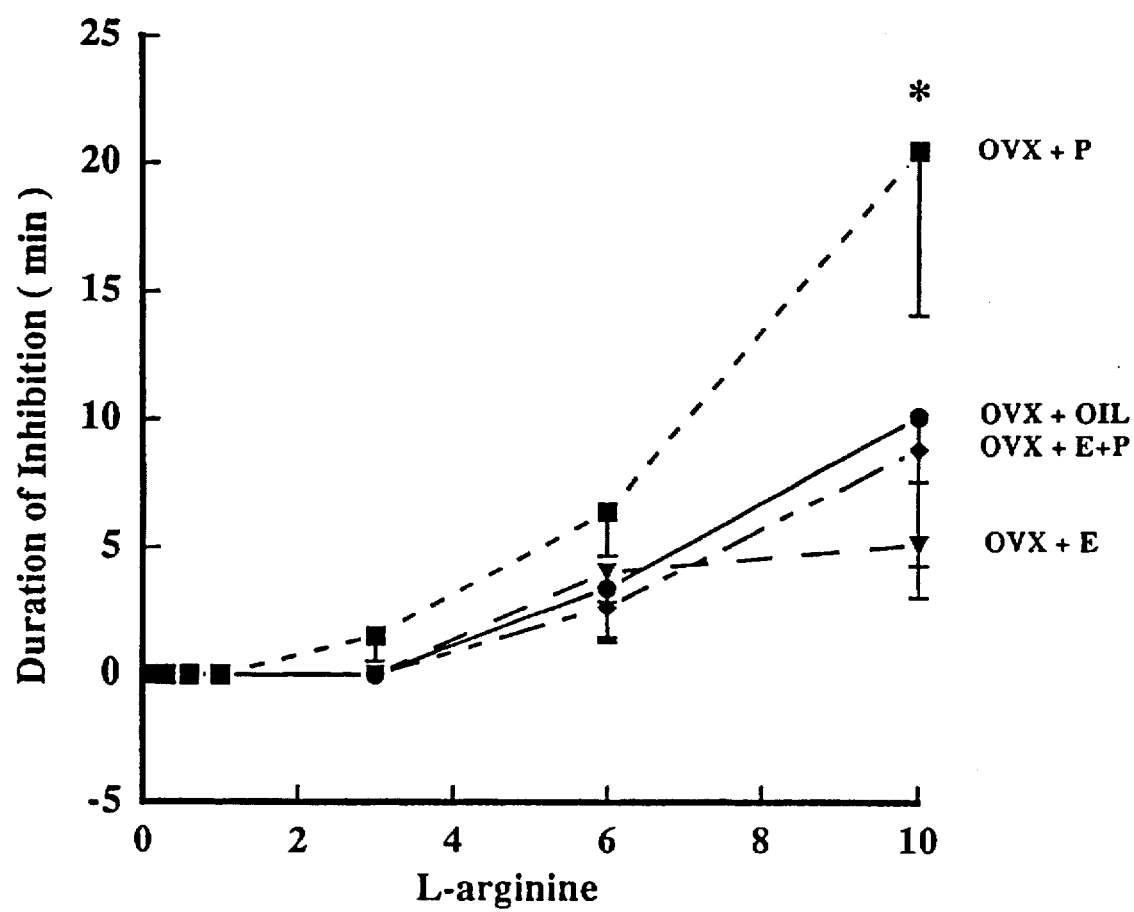
FIG. 3: Dose response effects of L-arginine (0.6 mM to 10 mM) on the spontaeous contractility of uterine strips from ovariectomized adult rats. Animals received s.c. injection of 1 µg estradiol—17b (OVX+E), 2 mg progesterone (OVX+ P), estradiol and progesterone (OVZ+E+P) in sesame oil or oil alone (OVX+Oil) for 3 days prior to contractility measurements. Values are mean ± SEM for 4 strips from each animal from 4 rats per group. Data are analyzed by repeated measures ANOVA on four groups. *P<0.05 OVX+P vs OVX+E.

In the experiments whose results are shown by the graph of FIG. 3, nonpregnant ovariectomized rats received s.c. injection of 1 µg estradiol-17-β (OVX+E), 2 mg progesterone (OVX+P), estradiol and progesterone (OVX+E+P) in sesame oil or oil alone (OVX+Oil) for 3 days prior to contractility measurements. Values are mean ± SEM for 4 strips from each animal from 4 rats per group. *P<0.05 OVX+P vs OVX+E.

Figure 4:
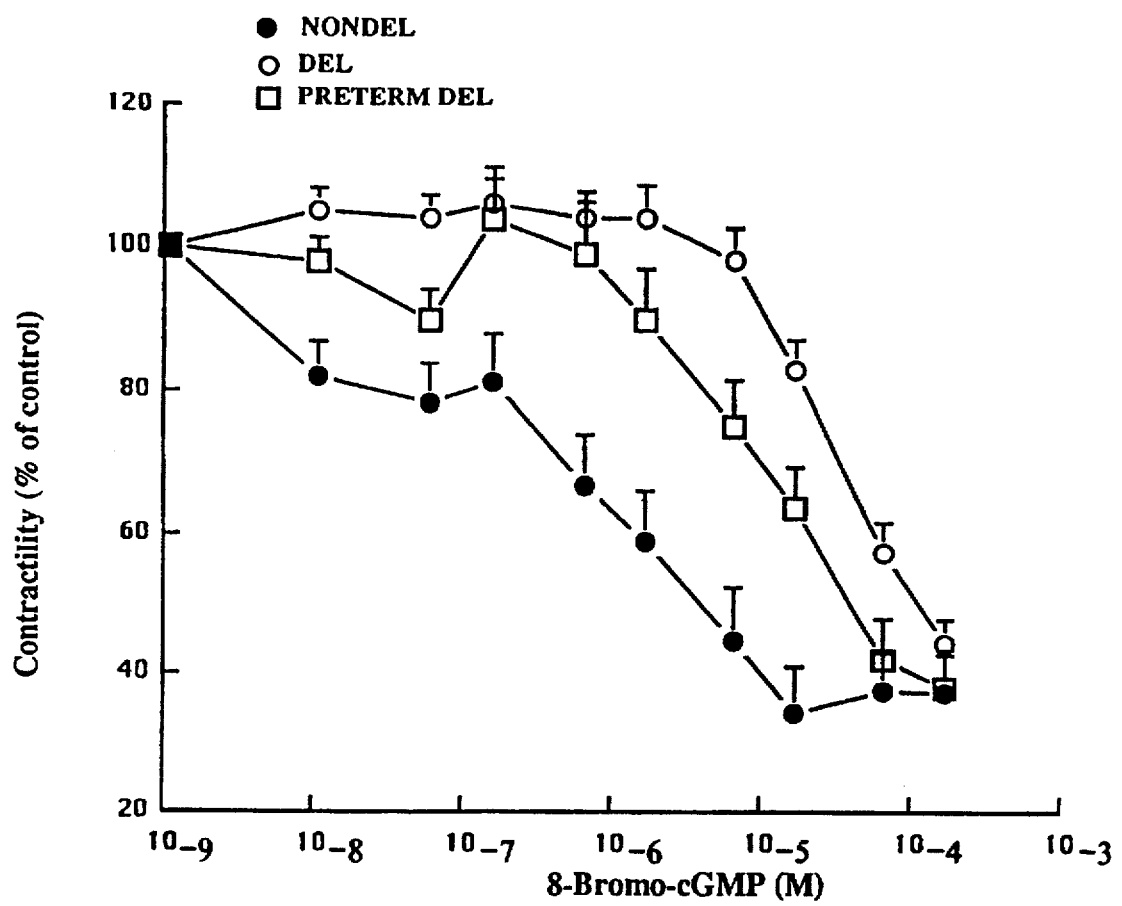
FIG. 4: 8-bromo-cGMP dose relaxation-response curves for uterine tissues from rats delivering, spontaeously at term (DEL), preterm with ZK299 (PRETERM DEL) and nondelivering (NONDEL) on day 18 of gestation. Each point represents mean ± SEM for 4 strips from each animal from 4 rats per group.

The charge of FIG. 4 shows 8-bromo-cGMP dose relaxation-response curves for uterine tissues from rats delivering, spontaneously at term (DEL), preterm with ZK299 (PRETERM DEL) and nondelivering (NONDEL)

on day 18 of gestation. Each point represents mean ± SEM for 4 strips from each animal from 4 rats per group.

The data in Table 1 below show the effects of L-NAME infusion on blood pressure (mm Hg) in pregnant rats.

TABLE 1

| | Blood Pressure (mm Hg) | | |
|---|---|---|---|
| | | L-NAME | |
| Gestation day | CONTROL | 25 mg/day | 50 mg/day |
| Day 15 | 121 ± 3[a] | 119 ± 2[a] | 123 ± 3[a] |
| Day 18 | 119 ± 3[a] | 144 ± 4[b] | 166 ± 2[c] |
| Day 22 | 120 ± 5[a] | 146 ± 2[b] | 168 ± 3[c] |

Means with different superscripts differ significantly (P<0.05)

The data in Table 2 below show the delivery and the pups delivered of L-NAME infusion to pregnant rats.

TABLE 2

| | | L-NAME | |
|---|---|---|---|
| | CONTROL | 25 mg/day | 50 mg/day |
| Day of Delivery | 22.3 ± 0.2 | 22.4 ± 0.2 | 22.7 ± 0.2 |
| Total # of pups | 59 | 65 | 56 |
| # of dead pups | 2 | 5 | 10 |
| Weight of pups | 6.32 ± 0.05[a] | 5.05 ± 0.08[b] | 4.56 ± 0.10[c] |
| Total # of animals | 8 | 9 | 10 |

Means with different superscripts differ significantly (P<0.05).

Figure 5:
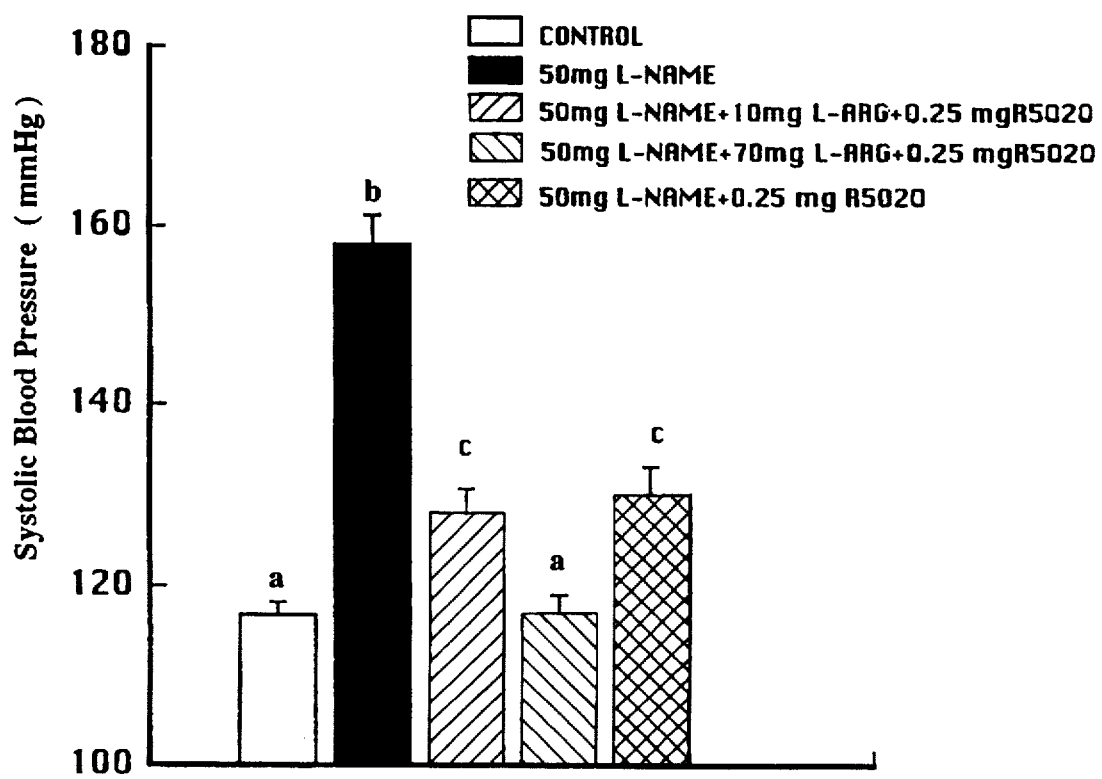
FIG. 5 is a bar chart which shows the effect on blood pressure of test animals of 50 mg of the hypertensive agent L-NAME, alone or in combination with one or both of L-arginine and progesterone (R-5020)

Another experiment using L-NAME-induced" preeclampsia" showed that treatment with L-arginine alone partially reduced blood pressure (FIG. 5). Similarly, animals treated with L-NAME and R 5020 (promegestone), a progestational agent with no antimineralocorticoid effect or other antagonistic or agonistic properties, also partially reduced L-NAME-induced hypertension. As also shown in FIG. 5, when the same doses of L-arginine and R 5020 were given simultaneously, their combined effect lowered blood pressure to normal levels.

Figure 6:
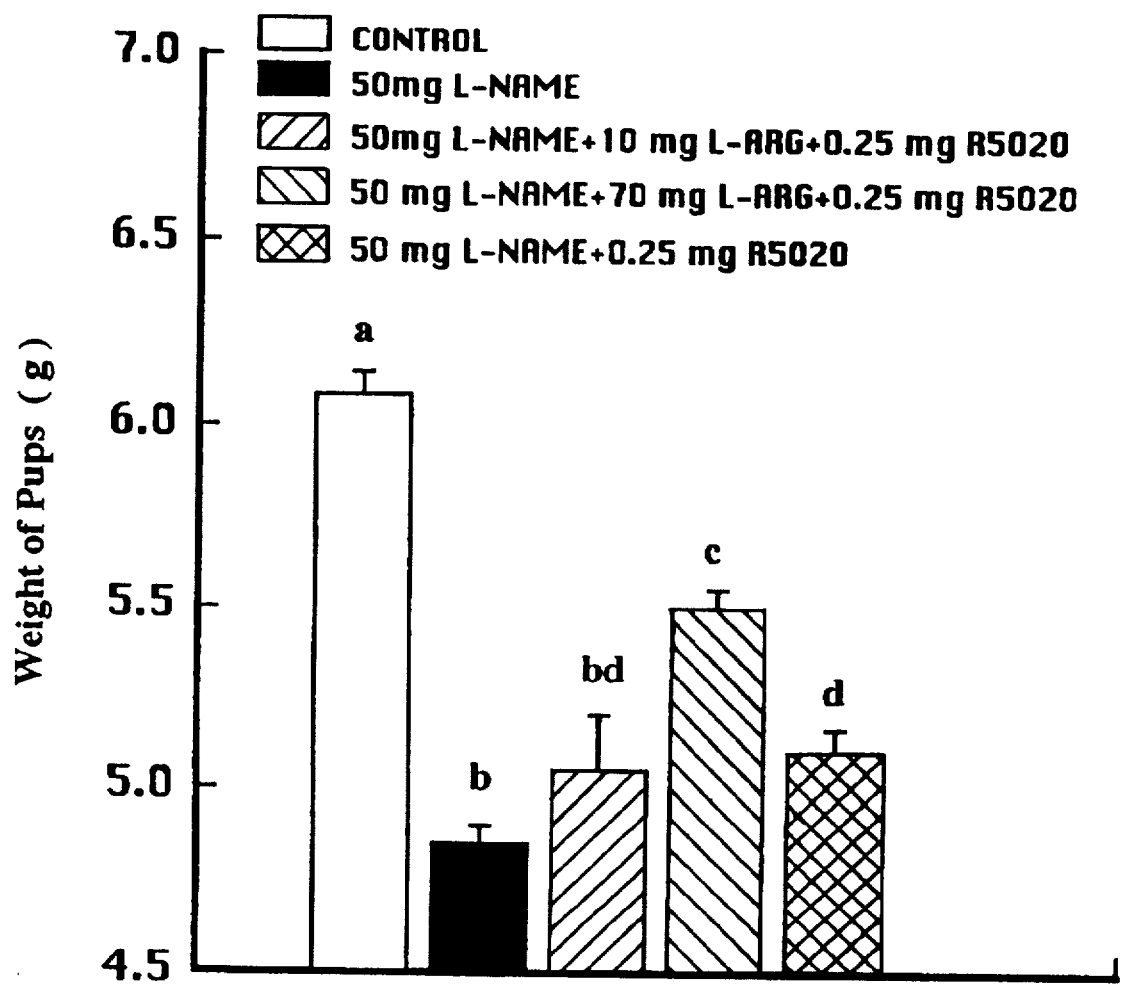
FIG. 6 is bar chart which shows the effect in the same experiments on pup weights of these compounds.

Additionally, evaluation of fetal weights in the same animals treated as described above, showed intrauterine fetal retardation (decreased weight of pups), typical preeclamptic fetuses (FIG. 6). Treatment of the "preeclamptic" groups of animals with either L-arginine alone or R 5020 alone slightly but statistically significant, elevated fetal weights. As also shown in FIG. 6, the combined effect of the two compounds administered together significantly elevated fetal weight above that observed with either compound alone, a highly significant advantage to survival of the fetus under these conditions.

It can be concluded from these studies that the combined treatment of L-arginine with a progestational agent whose activity is "pure", like R 5020 provides results which cannot be achieved with either type of drug alone. The studies show that the basis for this effectiveness lies in the ability of the progestional agent to increase the effectiveness of nitric oxide (or L-arginine, the substrate of nitric oxide) to dilate bood vessels and thereby lower blood pressure as well as increase fetalmaternal profusion, thereby increasing fetal weight.

The combined effect of the combination of these agents is surprisingly dramatic and, more importantly, the significant fetal and maternal effects observed with treatment with the combination. Prior medical evidence does not suggest that the combination would provide these advantages, because the basis for them is not the simple combination of two agonistic compounds but instead is the sensitizing of nitric oxide provided by the progestin. The studies clearly indicate that progestins increase the effector system for nitric oxide (not increase nitric oxide synthesis).

The method of treatment employed in this invention can also be employed for the treatment of hypertension (in both females and males), climacteric disorders (hot flashes, mood swings) in menopausal women, thrombotic disorders, menstrual disorders (dysmenorrhea, functional uterine bleeding), and hemorrhage, etc., following the dosage regime described herein.

Without further elaboration, it is believed that one skilled in the art can, using the preceding description, utilize the present invention to its fullest extent. The preferred specific embodiments are, therefore, to be construed as merely illustrative, and not limitative of the disclosure in any way whatsoever.

The entire disclosure of all applications, patents and publications, cited above and below are hereby incorporated by reference.

EXAMPLES

Example 1

Treatment of Preeclampsia

To a pregnant human female (ca 20–40 years; 60–80 kg) usually in her second half of pregnancy and displaying the symptoms of preeclampsia, including hypertension (above 140 mm systolic and above 90 mm diastolic), edema and protein-uria, administer 0.5 to 20 g of L-arginine and 200 mg of micronized progesterone per os daily in three divided doses until the symptoms are ameliorated. Thereafter, administer 0.5 to 5 mg of L-arginine and 60 mg of progesterone per os daily whenever the diastolic pressure rises above 80 mm; with increasing doses of L-argininine to from 5 to 20 mg daily until remission of the symptoms again occurs.

Example 2

Treatment of preeclampsia

To a human female comparable to and displaying the same symptoms as the one described in Example 1, administer daily 2×2.5 mg of nitroglycerine and 200 mg of progesterone following the same protocol, until the symptoms are ameliorated.

Example 3

Treatment of Preterm Labor

To a human female in her sixth month of pregnancy and displaying symptoms of a threatened spontaneous abortion, including blood spotting and periodic uterine spasms, administer daily 17 g of L-arginine and 50 mg of progesterone per os daily in three divided doses until the symptoms are ameliorated. Thereafter, administer 5 g of L-arginine and 50 mg of progesterone per os daily with increasing doses to 20 g of L-arigine daily until remission of the symptoms again occurs.

Example 5

Treatment of Preterm Labor

To a pregnant human female comparable to and displaying the same symptoms as the one described in Example 3, administer daily 2×25 mg of nitroglycerine and up to 180 mg of progesterone, following the same protocol, until the symptoms are ameliorated.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of treating preeclampsia accompanied or unaccompanied by preterm labor in a pregnant female mammal, which comprises administering to a female in need of such treatment (a) an effective amount of a progestin; and (b) an effective amount of nitric oxide synthase substrate, an effective amount of a nitric oxide donor, or both; and optionally, further comprising administering effective amounts of one or more agents selected from the group consisting of a cyclooxygenase inhibitor, a $PGI_2$-mimetic, a thromboxane ($TXA_2$) inhibitor, a compound possessing $PGI_2$-agonistic and $TXA_2$-inhibiting properties, a compound possessing $TXA_2$-antagonistic and $PGI_2$-mimetic activities, and a $TXA_2$-antagonist.

2. The method of claim 1, wherein the female mammal is a human suffering from preeclampsia unaccompanied by preterm labor.

3. The method of claim 1, wherein the female mammal is a human also exhibiting symptoms of preterm labor.

4. The method of claim 1, wherein the female mammal is a human and a nitric oxide synthase substrate is administered thereto.

5. The method of claim 4, wherein the substrate is L-arginine.

6. The method of claim 1, wherein the female mammal is a human and a nitric oxide donor is administered thereto.

7. The method of claim 6, wherein the nitric oxide donor is sodium nitroprusside, nitroglycerin, glyceryltrinitrate, SIN-1, isosorbidmononitrate or isosorbiddinitrate.

8. The method of claim 6, wherein the nitric oxide donor is administered orally.

9. The method of claim 1, wherein the female mammal is a human and the nitric oxide substrate or donor is administered thereto in combination with a cyclooxygenase inhibitor.

10. The method of claim 9, wherein the inhibitor is aspirin.

11. The method of claim 1, wherein the female mammal is a human and the nitric oxide substrate or donor is administered thereto in combination with a $PGI_2$-mimetic.

12. The method of claim 11, wherein the $PGI_2$-mimetic is iloprost or cicaprost.

13. The method of claim 1, wherein the female mammal is a human and the progestin administered thereto is progesterone.

14. A method of treating preeclampsia accompanied or unaccompanied by preterm labor in a pregnant female mammal comprising administering an effective amount of a nitric oxide synthase substrate, a nitric oxide donor or both.

15. A method of claim 14, comprising administering a nitric oxide synthase substrate.

16. A method of claim 15, wherein the substrate is L-arginine.

17. A method of claim 14, wherein the female is a human.

18. A method of claim 14, wherein a nitric oxide donor is administered.

19. A method of claim 18, wherein the nitric oxide donor is sodium nitroprusside, nitroglycerin, glyceryltrinitrate, SIN-1, isosorbidmononitrate or isosorbiddinitrate.

20. A method of claim 14, wherein the synthase substrate or donor is administered orally.

21. A method of claim 15, wherein the amount of nitric oxide synthase substrate is effective to raise the blood level of circulating L-arginine to at least about 1 mmole above the normal circulating level of L-arginine.

22. A method of claim 18, wherein the amount of nitric oxide donor is effective to provide a blood level of such donor of about 1–1000 nmole.

* * * * *